(12) United States Patent
Meurs et al.

(10) Patent No.: US 6,172,182 B1
(45) Date of Patent: Jan. 9, 2001

(54) PROCESS FOR THE MANUFACTURE OF EPOXY COMPOUNDS

(75) Inventors: Jan Hermen Hendrik Meurs; Jozef Jacobus Titus Smits; Judith Johanna Berendina Walhof, all of Amsterdam (NL)

(73) Assignee: Shell Oil Company, Houston, TX (US)

( * ) Notice: Under 35 U.S.C. 154(b), the term of this patent shall be extended for 0 days.

(21) Appl. No.: 09/133,746

(22) Filed: Aug. 13, 1998

(30) Foreign Application Priority Data

Aug. 14, 1997 (EP) .................................................. 97202519

(51) Int. Cl.⁷ ............................. C08G 65/26; C08G 65/28
(52) U.S. Cl. ......................... 528/421; 528/307; 528/360; 528/364; 528/419
(58) Field of Search ................... 528/307, 360, 528/364, 419, 421

(56) References Cited

U.S. PATENT DOCUMENTS

| 2,856,413 | 10/1958 | Malkemus et al. | 260/348 |
| 4,276,223 | 6/1981 | Wu | 260/348.16 |
| 4,390,732 | 6/1983 | Merk et al. | 568/648 |

FOREIGN PATENT DOCUMENTS

| 46455 | 3/1966 | (DE) . | |
| 1940205 | 8/1969 | (DE) | C07D 000/00 |
| 4213010 | 10/1993 | (DE) | C07D 303/04 |
| 47473 | 9/1981 | (EP) | C07D 301/02 |
| 57-077682 | 5/1982 | (JP) | C07D 301/02 |
| 61-033180 | 2/1986 | (JP) | C07D 301/02 |

OTHER PUBLICATIONS

Patent Abstracts of Japan vol. 010, No. 136 (C–347) May 20, 1986 & JP 60 260568 A (Daicel Kagaku Kogyo KK), Dec. 23, 1985, see abstract.

*Primary Examiner*—Robert Dawson
*Assistant Examiner*—Jeffrey B. Robertson

(57) ABSTRACT

Process for the manufacture of epoxy compounds having the formula

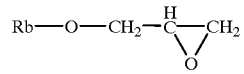

wherein Rb represents a group selected from those of the formulae

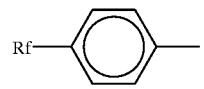

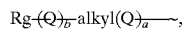

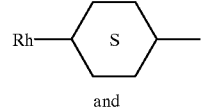

and

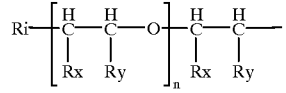

by reaction of a compound

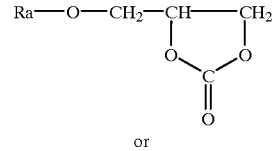

or

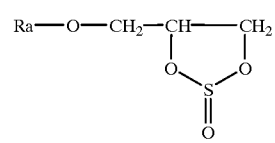

with an alkylene oxide, in the presence of a certain catalyst.

9 Claims, 2 Drawing Sheets

PROCESS FOR THE MANUFACTURE OF EPOXY COMPOUNDS

The invention is relating to a process for the manufacture of epoxy compounds. More in particular the invention is relating to a process for the manufacture of epoxy compounds without the involvement of halogen and in particular chlorine gas.

Epoxy compounds, which are manufactured in a great variety on large industrial scales throughout the world, are used for an extensive scale of end applications, such as the manufacturing of shaped articles, including embedded small electronic components such as semi-conductors or chips and the prepregs for the subsequent manufacture of printed circuits for the electronic industry, coatings including the organic solvent based coatings as well as the more modern aqueous epoxy resin dispersion coatings, and in particular can and drum coatings, composites and laminates showing great flexibility, and the like.

Said starting epoxy compounds were manufactured up to now by means of the starting reagent epihalohydrin and in particular epichlorohydrin, which in its turn was manufactured via allylchloride, prepared from propene and gaseous chlorine.

It will be appreciated that on the one hand, there has been developed in the last decade and in particular in the last five years, an increasing pressure from national or regional governmental regulations and requirements to chemical process industry, in order to drastically reduce possible chlorine emissions or even to avoid the use of chlorine completely, and on the other hand, in the current manufacturing processes for chlorination of propene in the gaseous phase there is still a need to improve the relatively low yield and to diminish the high fouling tendency.

Moreover, during the reaction of epihalohydrin with phenolic compounds to form epoxy resin it is not possible to avoid completely that halogen, originating from the epihalohydrin, is intermingled in a resin as a product in the form that the halogen atom is chemically bound to the epoxy resin itself.

As one of the important applications of the epoxy resin is encapsulation of micro electronic material, it will be appreciated that this intermingled halogen liberates as an acid by moisture, during use of the final article for a long period of time and this acid leads to corrosion of a metal material.

Therefore one object of the present invention is formed by a process, meeting the requirements of the application conditions and of the present environmental legislation and that one presumably enforced in the near future, and starting from cheap and generally available basic chemicals.

One of the alternative manufacturing routes for epoxy resins, proposed in the past was that according the following simplified reaction scheme:

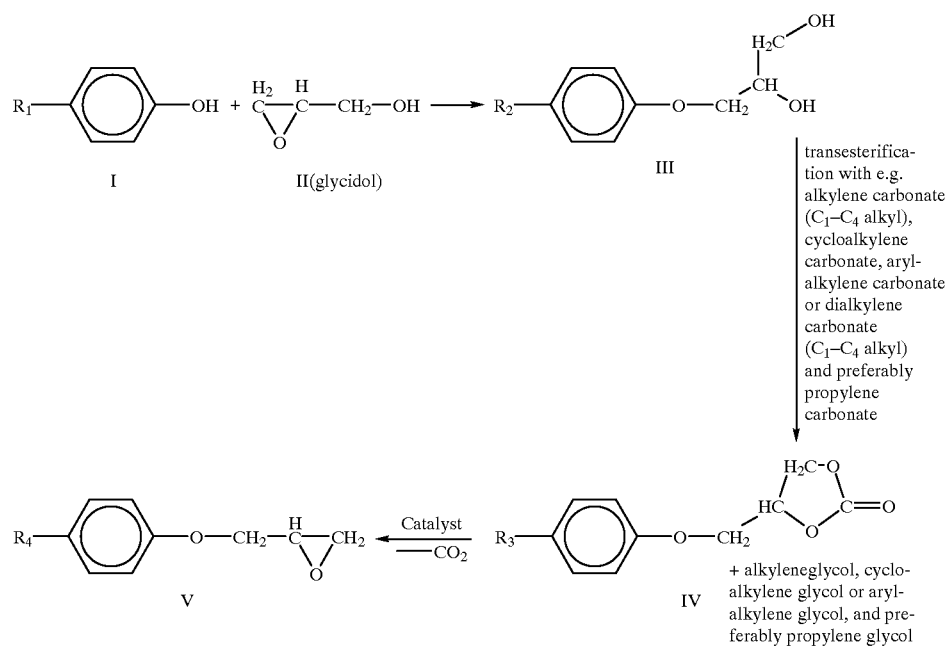

wherein $R_1$ represents a residue comprising one or more additional phenol groups, wherein $R_2$ represents a residue comprising one or more additional groups of the formula.

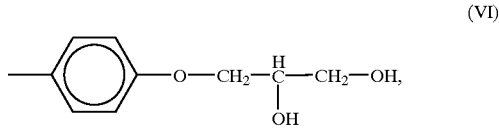

(VI)

wherein $R_3$ represents a residue comprising one or more additional groups of the formula:

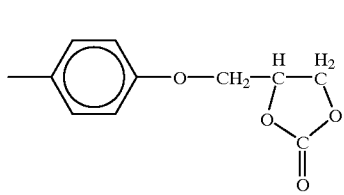

(VII)

and wherein $R_4$ represents a residue comprising one or more additional groups

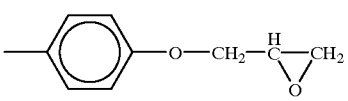

(VIII)

Although it was already known from e.g. Japanese patent application Sho 61-33180 A, to produce epoxy compounds by decarboxylating a carbonate compound, using as catalyst a combination of an alkali metal halide and of a dihydrogenphosphate of an alkali metal while earlier proposed similar processes were known from e.g. JP-Sho-57-77682 A and U.S. Pat. No. 2,856,413, said route could not be used for economical manufacture of epoxy compounds up to now.

In particular from JP-Sho-61-33180 it will be appreciated that the finally obtained mono-epoxy compounds had such a simple molecular structure, that they could be recovered from the initially crude reaction mixture by distillation.

However such a distillation has appeared to be not possible for the commercial standard difunctional and multifunctional epoxy compounds aimed at.

Therefore there was still a strong need for improvement of this proposed route to enable industrial scale manufacture at all.

As a result of extensive research and experimentation it has now been surprisingly found, that compounds of the formula

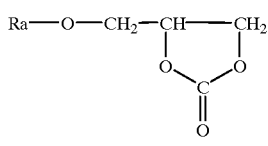

(A)

or

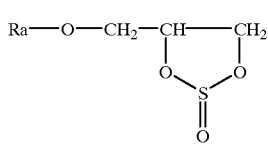

(B)

wherein Ra represents
(1) a group

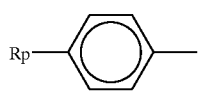

wherein Rp represents hydrogen
or a residue, comprising one or more additional groups of the formula

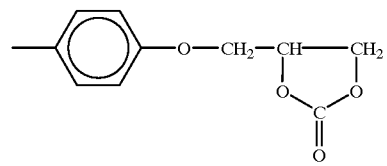

or

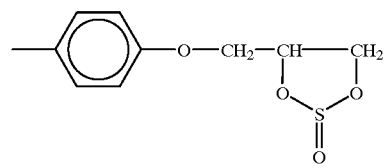

(2) a group $Rq\text{-}(Q)_b\text{-alkyl-}(Q)_a\text{-}$ wherein the alkyl group is straight or branched and contains from 2 to 30 carbon atoms wherein Q is aryl of from 6 to 20 carbon atoms (preferably phenyl) or cycloalkyl from 6 to 20 carbon atoms (preferably cyclohexyl) and a and b are 0 or 1, wherein Rq represents hydrogen or a residue, comprising one or more additional groups of the formula

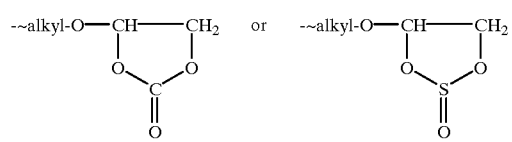

(3) a group

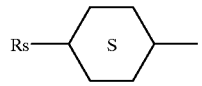

wherein Rs represents hydrogen or a residue comprising one or more additional groups of the formula

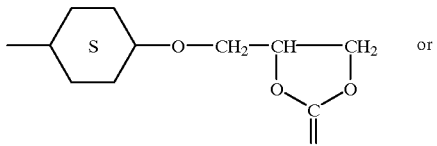

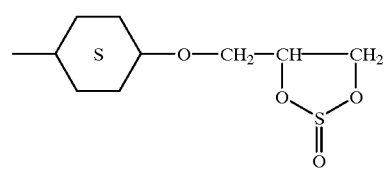

(4) a group

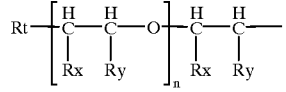

wherein Rt represents hydrogen or a residue comprising one or more additional groups of the formula:

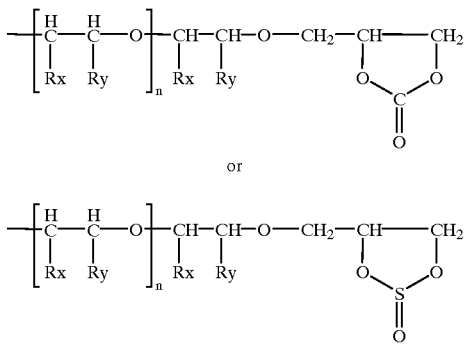

or wherein Rx and Ry may represent hydrogen or only one of the symbols Rx and Ry may represent alkyl, having from 1 to 4 carbon atoms (preferably methyl), wherein n is an integer from 1 to 100 and preferably from 5 to 50, can be very efficiently reacted with alkylene oxide having from 1 to 20 carbon atoms (preferably from 1 to 4 carbon atoms), in the presence of a catalyst, selected from the group of compounds containing at least one cation:

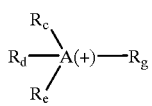
(C)

wherein A represents nitrogen or phosphorus and preferably phosphorus, wherein $R_c$, $R_d$ and $R_e$ each represent an optionally substituted alkyl group having 1 to 10 carbon atoms and preferably from 1 to 4, or an optionally substituted phenyl group and wherein $R_g$ represents an alkyl group having from 1 to 6 carbon atoms which may optionally be terminally substituted by an aryl group (preferably phenyl) or by a group of formula,

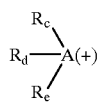
(C')

in combination with a counter anion $X^-$ selected from halogen, acetate, phosphate or carboxylate or combinations thereof, to form alkylene carbonate or alkylene sulfite and a compound

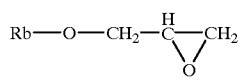
(D)

wherein Rb represents
(1) a group

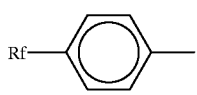

wherein Rf represents hydrogen or a residue comprising one or more additional groups of the formula

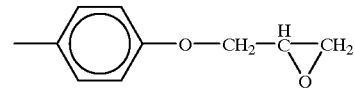

(2) a group $Rj$-$(Q)_b$-alkyl-$(Q)_a$-, wherein the alkyl group is straight or branched and contains from 2 to 30 carbon atoms, wherein Q is aryl of from 6 to 20 carbon atoms (preferably phenyl) or cycloalkyl from 6 to 20 carbon atoms (preferably cyclohexyl) and a and b are 0 or 1,
wherein Rj represents hydrogen or a residue comprising one or more additional groups of the formula:

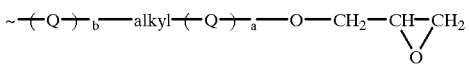

(3) a group

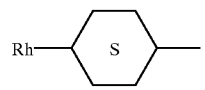

wherein Rh represents hydrogen or a residue comprising one or more additional groups of the formula

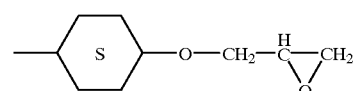

(4) a group

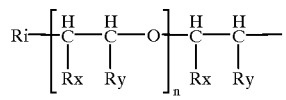

wherein Rx and Ry are as defined hereinbefore and Ri represents hydrogen or a residue comprising one or more additional groups of the formula

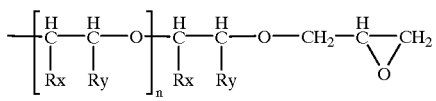

According to a preferred embodiment of this process step, the counter anion is selected from halogen and more preferably this counter anion is chlorine.

The substituents of the alkyl groups or phenyl groups $R_c$, $R_d$ and $R_e$ may be selected from halogen, nitro, alkyl or alkoxy having from 1 to 4 carbon atoms, carboxyl or sulphonic acid groups. More preferably the alkyl or phenyl groups $R_c$, $R_d$ and $R_e$ are unsubstituted or the phenyl groups are monosubstituted on the ortho place.

Figure 1:
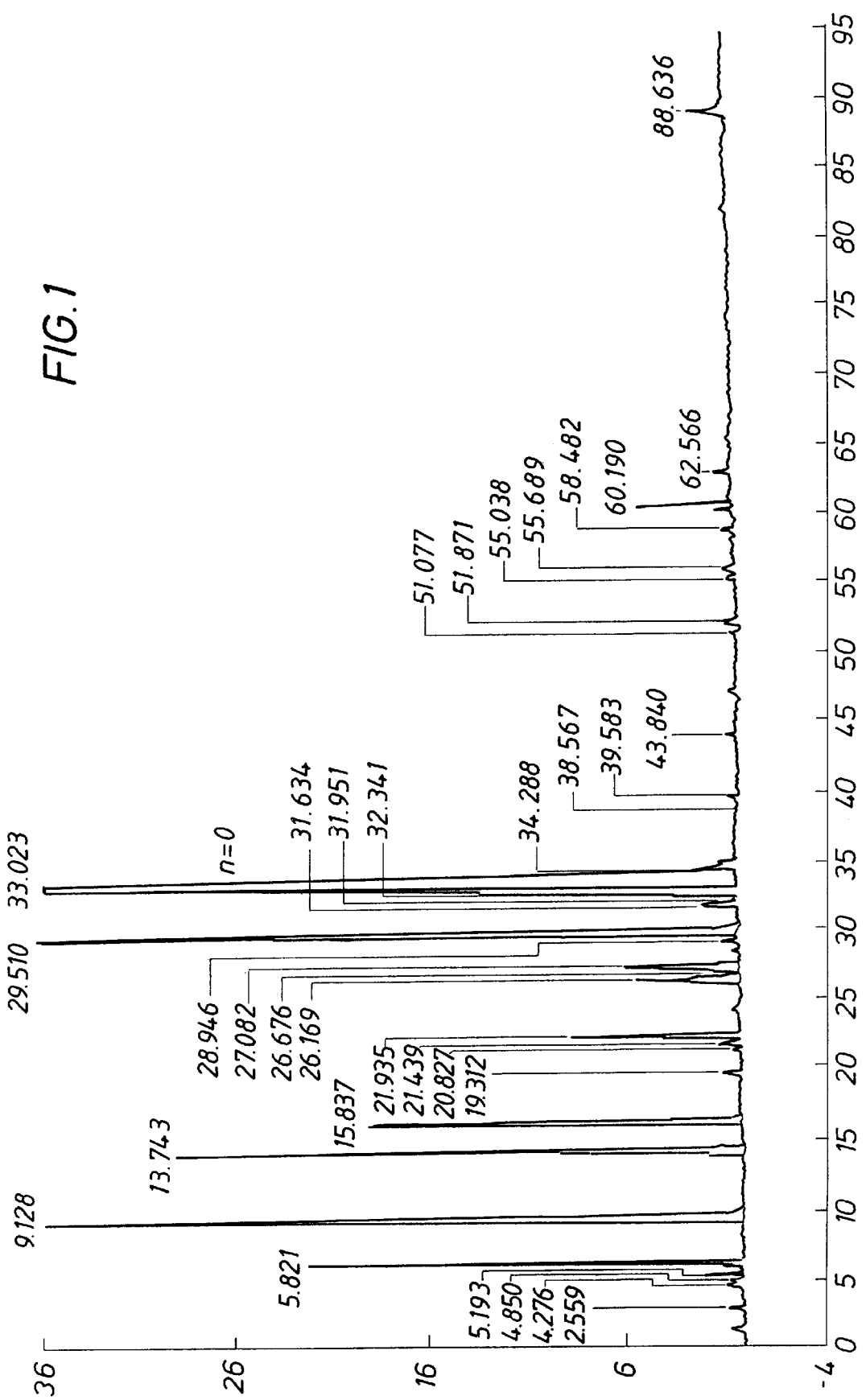
FIG. 1 is a liquid chromatograph of an epoxy resin according to the present invention.
Figure 2:
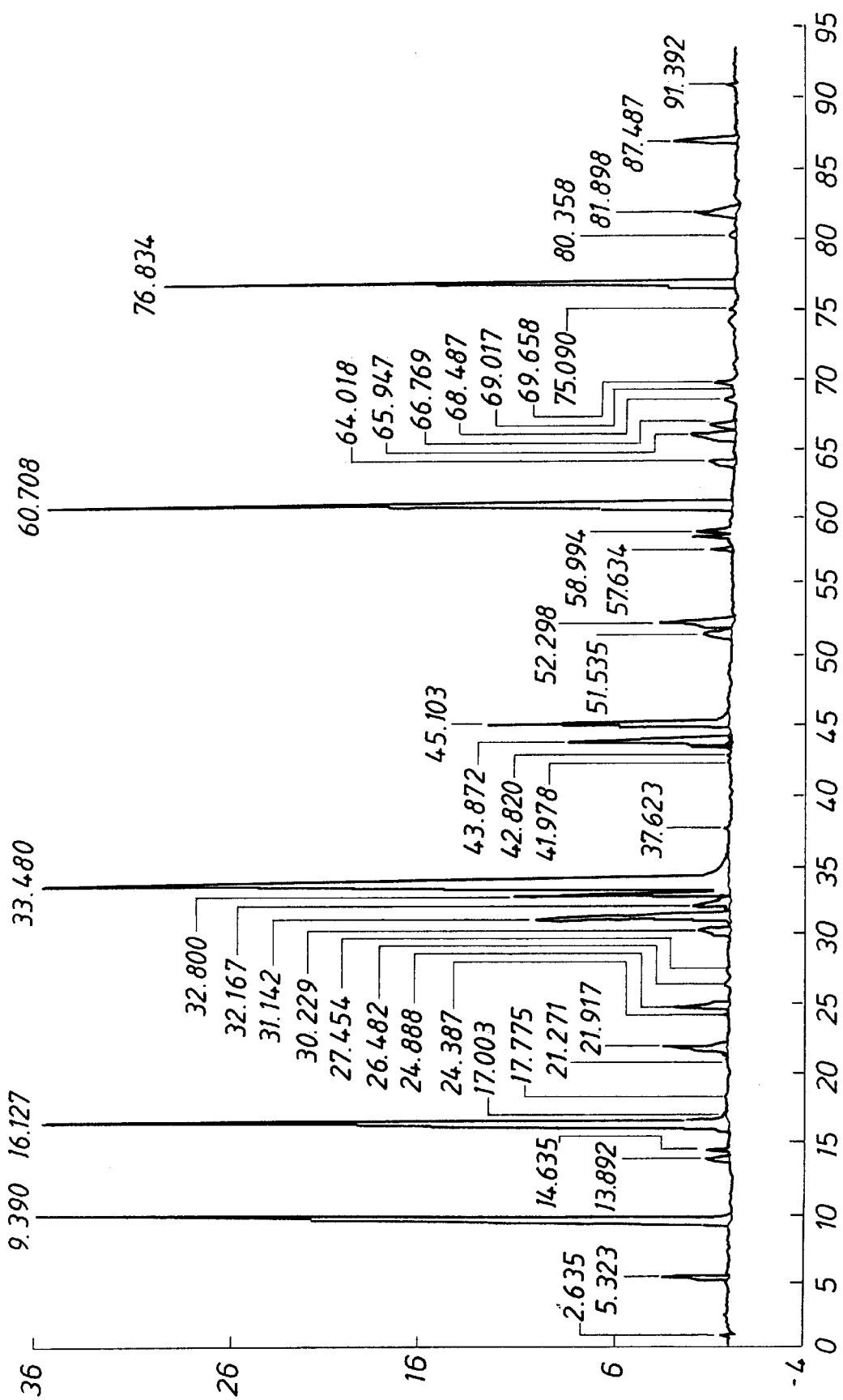
FIG. 2 is a chromatogram of a standard epoxy resin.

According to further preferred embodiments of the hereinbefore described reaction ethyltriphenylphosphonium chloride, ethyltri(orthotolyl)phosphonium chloride or ethyltriphenylammonium chloride are used as catalysts. As most preferred catalyst ethyltriphenylphosphonium chloride is used.

In general the hereinbefore specified reaction (process step) is carried out at temperature in the range of from 100 to 250° C., and preferably from 130 to 200° C. and at a pressure in the range of from 1 to 30 bar and preferably from 15 to 25 bar. During said reaction an excess of alkylene oxide is used with reference to the molar amount of the compounds (A) or (B). The applied excess of alkylene oxide can be in the range of from 10 to 100% of the equimolecular amount and preferably in the range of from 20 to 60%.

According to a particular embodiment of the hereinbefore specified conversion step, compounds of the formulae

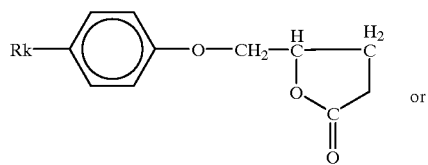

(E)

or

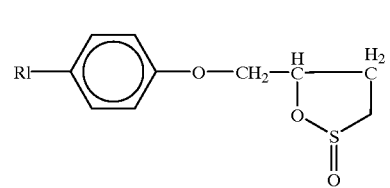

(F)

wherein Rk represents a residue, comprising one or more additional groups of the formula

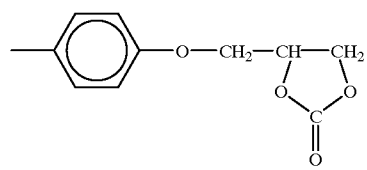

(E')

and wherein Rl represents a residue comprising one or more additional groups of the formula

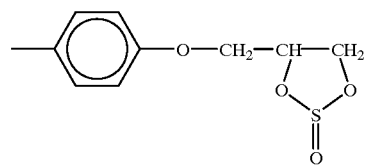

(F')

are reacted with alkylene oxide having from 1 to 10 carbon atoms, in the presence of a catalyst, selected from the group of compounds containing at least one cation:

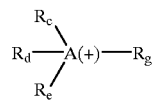

(C)

wherein A represents nitrogen or phosphorus and preferably phosphorus, wherein $R_c$, $R_d$ and $R_e$ each represent an optionally substituted alkyl group having 1 to 10 carbon atoms and preferably from 1 to 4, or an optionally substituted phenyl group and wherein $R_g$ represents an alkyl group having from 1 to 6 carbon atoms which may optionally be terminally substituted by an aryl group (preferably phenyl) or by a group of formula,

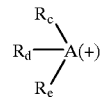

(C')

in combination with a counter anion X⁻ selected from halogen, acetate, phosphate or carboxylate or combinations thereof, to form alkylene carbonate or alkylene sulfite and a compound

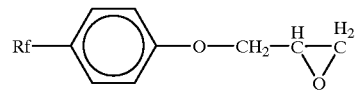

(D')

More in particular the specified conversion step can be carried out starting from compounds

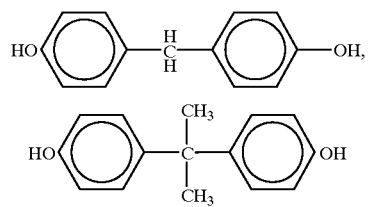

or halogenated, in particular brominated derivatives thereof, but also starting from polymeric compounds, such as phenolic formaldehyde condensation polymers, containing a greater number of phenolic groups, which may partially or completely be converted into the groups of the formula

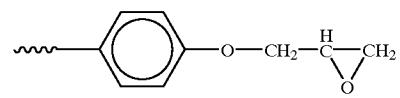

It will be appreciated that not only relatively simple compounds, such as

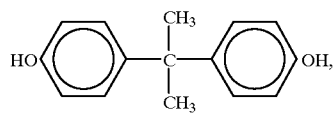

-continued

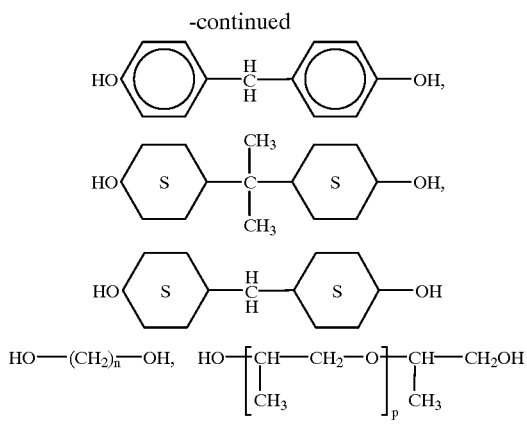

wherein n and p are integers from 5 to 50, but also polymeric compounds, containing a greater number of hydroxyl groups which may be completely or partially be converted into groups

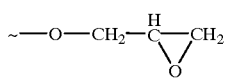

i.e. the simple standard commercial epoxy compound of formula

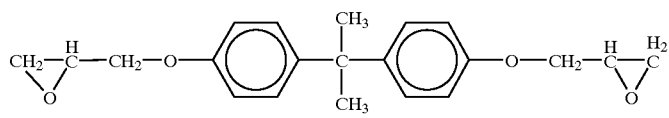

can be prepared according to the process of the present invention, but also commercial a multifunctional epoxy compound, having a much more complicated structure can be prepared.

For example in this respect, a great variety of phenol-formaldehyde resins can be used as starting material I (novolac resins).

It was known for a long time to carry out the industrial scale manufacture of compound I starting from a ketone and phenol, representing cheap products.

An important representative of compound I, having a rather simple structure is DPP (diphenylolpropane).

Also the reagent II (glycidol) can be regarded as a relative cheap product prepared from propene.

It will be appreciated that the invention is also relating to a complete integrated manufacturing process for the final epoxy resins, comprising the hereinbefore specified process step, and starting from a polyphenol compound I, such as DPP for standard commercial epoxy resins, and glycidol (II).

Accordingly the invention also relates to a process for the manufacture of epoxy compounds comprising the steps of:

(a) conversion of propylene into propylene oxide, its re-arrangement into allylalcohol and its subsequent oxidation into glycidol, in the presence of a heterogeneous catalyst comprising at least a transition metal such as titanium, vanadium or molybdenum, as such or in the form of a compound of said metals dispersed in a chemically inert carrier, or in the presence of a homogeneous catalyst formed by a dissolved or dispersed compound of said metals, (b) reaction of a phenolic compound (I)

with glycidol

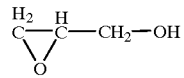

into di-α-glycol

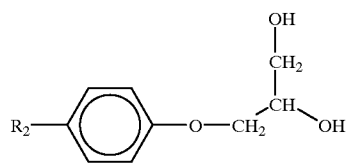

(c) reaction of di-α-glycol (II) with alkylenecarbonate, or alkylene sulfite, and preferably propylene carbonate or ethylene carbonate, into the compound (A)

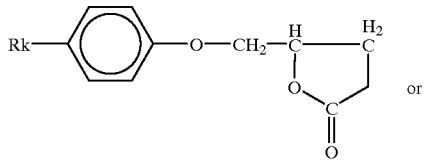

or

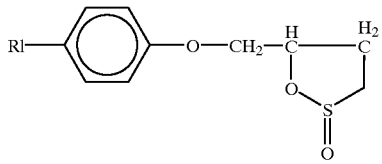

(d) reaction of compound (E) or (F) with alkylene oxide, having from 1 to 20 carbon atoms and preferably from 1 to 4 carbon atoms, in the presence of a catalyst, selected from the group of compounds containing at least one cation:

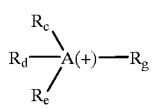

wherein A represents nitrogen or phosphorus and preferably phosphorus, wherein $R_c$, $R_d$ and $R_e$ each represent an optionally substituted alkyl group of from 1 to 10 carbon atoms or an optionally substituted phenyl group and wherein $R_g$ represents an alkyl group having from 1 to 6 carbon atoms which may optionally be terminally substituted by an aryl group (preferably phenyl) or by a group of formula

(C')

together with a counter anion selected from halogen, acetate, phosphate or carboxylate or combinations thereof, to form alkylene carbonate or alkylene sulfite and a compound

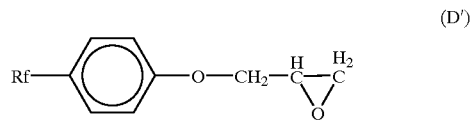

(D')

The oxidation step to form glycidol occurring in step (a) is preferably carried out in the presence of a catalyst comprising titanium dispersed in silica or vanadium on silica.

Another aspect of the present invention is formed by the final epoxy resins, which contain only traces of intermingled halogen and in particular chlorine, which are obtainable by the complete integrated manufacturing process as specified hereinbefore and which show a significantly deviating molecular structure as compared with those of the conventional epoxy resins.

Said characteristic molecular structure of the novel epoxy resins are clearly expressed by HPLC diagrams made of these resins and by a total halogen, and in particular chlorine content, of below 1300 ppm.

More in particular the novel epoxy resins, containing only traces of intermingled halogen below 1000 ppm and in particular in the range of from 300 to 1000 ppm, can be characterized by the hereinafter specified HPLC signals.

Said halogen contents are significantly lower than the usual range of from 1400 to 1800 of conventional resins.

The epoxy resins according to the present invention were characterized by HPLC analysis using a HP1090 liquid chromatograph (as depicted in Fig. I). For comparison, also a chromatogram was taken from a standard epoxy resin (as depicted in Fig. II).

2.0 Gram of the resin was dissolved in 20 grams acetonitrile. Anisole was used as an internal standard. The analysis was performed using a Novapak C18 column, 15 cm×3.9 cm, Waters. The flow was 1 ml/min, injection volume was 1 microliter. The initial solvent composition consisted of 75% water and 25% acetonitrile. A solvent gradient was used.

In 110 min the composition changed linear to 6.5% water and 93.5% acetonitrile

At 115 min: 0% water, 100% acetonitrile

At 125 min: 75% water, 25% acetonitrile

At 130 min: 75% water, 25% acetonitrile

The analysis was performed at 50° C., with UV detection at 275 nm.

The chromatogram clearly shows the absence of the so-called build-up products (n=1, n=2, etc.) that are normally present in resins prepared from bisphenol A and epichlorohydrin (Peaks at 60.7 min and 76.8 min). In addition, some extra peaks emerge in the chromatogram (27 min, the cyclic biscarbonate ester; 30.5 min, a compound with one carbonate group and one epoxy group), 5.8 min (bis-α-glycol), 13.7 min, and 15.8 min. These last two peaks do not occur in the chromatogram of standard epoxy resins (Fig. II). Besides these mentioned peaks there is a large number of differences between the two chromatograms.

It will be appreciated that the exact retention times can vary somewhat between experiments.

The invention is further illustrated by the following examples and comparative examples, however, without restricting its scope to these specific embodiments.

Preparation of the Bis-α-glycol Ether of DPP

Compound 1

EXAMPLE 1

In a 100 ml three-necked round-bottom flask equipped with a reflux condenser and a thermocouple, 22.84 gram (0.100 mol) diphenylolpropane (DPP or bisphenol A) and 15.54 gram glycidol (0.210 mol) is dissolved in 15.05 gram (0.150 mol) methylisobutylketone (MIBK) and 15.04 (0.25 mol) isopropylalcohol (IPA). Then 10.80 gram (0.100 mol) anisol was added as an internal reference compound. At 80° C. 6 mol % of an aqueous NaOH solution (50 wt %) was added at once. The mixture was maintained at 80° C. for 6 hours. Then, the solvent was removed in vacuo. The bis-α-glycol ether of DPP (1) is obtained as a white solid material (33.9 gram, 89.5%).

The material is analysed by High Pressure Liquid Chromatography. Sideproducts are: the so-called build-up product (one extra glycidol group added), the 1,2-OH (resulting from incomplete conversion, and the 1,2-1,3, which is a compound that bears a 1,3-propane diol moiety.

Examples 2 to 19 are summarized in the table.

TABLE

| | Reaction conditions and molar ratio's of reaction products | | | | | | |
|---|---|---|---|---|---|---|---|
| glycidol/DPP molar ratio | solvent (mol %) | temp. (° C.) | catalyst (mol %) | diα.gc (mol %) | 1,2–1,3 (mol %) | 1,2-OH (mol %) | build-up (mol %) |
| 2.2 | MIBK 300 | 70 | NaOH 2 | 79.9 | 3.4 | 12.8 | 3.4 |
| 2.2 | MIBK 300 | 90 | NaOH 2 | 85.7 | 4.9 | 0.0 | 9.1 |
| 2.1 | MIBK 300 | 90 | NaOH 2 | 87.9 | 4.6 | 2.6 | 4.9 |

TABLE-continued

Reaction conditions and molar ratio's of reaction products

| glycidol/DPP molar ratio | solvent (mol %) | temp. (° C.) | catalyst (mol %) | diα.gc (mol %) | 1,2–1,3 (mol %) | 1,2-OH (mol %) | build-up (mol %) |
|---|---|---|---|---|---|---|---|
| 2.1 | MIBK 300 | 70 | NaOH 6 | 89.6 | 3.9 | 2.5 | 4.0 |
| a2.1 | MIBK 300 | 90 | NaOH 2 | 88.2 | 4.7 | 1.9 | 5.2 |
| 2.2 | MIBK 150 IPA 250 | 70 | NaOH 2 | 51.9 | 2.0 | 43.8 | 1.4 |
| 2.1 | MIBK 150 IPA 250 | 70 | NaOH 6 | 84.0 | 3.4 | 9.0 | 3.4 |
| 2.1 | MIBK 150 IPA 250 | 80 | NaOH 2 | 71.1 | 3.3 | 21.9 | 3.0 |
| 2.1 | MIBK 150 IPA 250 | 80 | NaOH 6 | 89.5 | 4.1 | 1.7 | 4.7 |
| 2.1 | MIBK 230 IPA 125 | 70 | NaOH 6 | 80.2 | 3.5 | 12.7 | 3.3 |
| 2.1 | MIBK 270 IPA 45 | 70 | NaOH 6 | 88.0 | 3.7 | 2.3 | 6.1 |
| 2.1 | MIBK 180 IPA 35 | 70 | NaOH 6 | 87.0 | 3.8 | 4.4 | 4.8 |
| b2.2 | MIBK 185 IPA 35 | 70 | NaOH 6 | 84.0 | 5.5 | 4.6 | 5.7 |
| 2.04 | MIBK 200 | 100 | NaOH 2 | 84.0 | 5.5 | 4.6 | 5.7 |
| 2.03 | MIBK 200 | 90 | NaOH 2 | 83.9 | 4.8 | 5.6 | 5.3 |
| 2.04 | MIBK 200 | 90 | $Na_2CO_3$ 2 | 68.4 | 3.4 | 24.3 | 2.8 |
| 2.04 | MIBK 200 | 80 | NaOH 2 | 69.3 | 3.6 | 22.5 | 3.5 |
| c2.05 | MIBK 200 | 90 | $Na_2CO_3$ | 81.3 | 4.7 | 8.6 | 4.9 |

If the reaction is performed in pure MIBK (without IPA as a co-solvent), the bis-α-glycol ether of DPP (1) crystallises after cooling down.

Preparation of the Bis-cyclic Carbonate Ester of DPP

Compound 2

EXAMPLE A

A 100 ml round-bottom flask is charged with 20.0 gram of the bis-glycol ether of DPP (89% pure, 47.3 mmol) and 28.58 gram (0.280 mol) propylenecarbonate. The mixture is heated at 100° C. and 2 mol % of an aqueous NaOH solution (50 wt %) is added. After 1 hour, a vacuum is applied to remove the formed propanediol and excess propylenecarbonate (final conditions 160° C., 20 mbar). The compound is suspended in water, filtered and dried. The yield of the solid white material is 22.4 gram.

EXAMPLE B

The same procedure as in example A, however with a larger excess of propylenecarbonate (15 fold excess). The distillation was performed using a Vingreux distillation column. HPLC analysis proved that the selectivity enhanced by this procedure. The compound is suspended in water, filtered and dried. The yield of the solid white material is 22.2 gram.

EXAMPLE C

The same procedure as in example B was used. The solid product was heated with acetonitrile until it was almost completely dissolved. After cooling down the material crystallises. The compound is suspended in water, filtered and dried. The selectivity to the bis-cyclic carbonate ester is almost 90%.

Preparation of the Bis-cyclic Carbonate Ester of DPP

EXAMPLE D

In a 100 ml three-necked round-bottom flask equipped with a reflux condenser and a thermocouple, 22.84 gram (0.1 mol) diphenylolpropane (DPP or bisphenol A) and 15.12 gram (0.204 mol) glycidol is dissolved in 30.63 gram (0.3 mol) propylene carbonate (PC). At 50° C. 0.48 gram 50 wt % NaOH (aq) (6 mol% on DPP) is added dropwise. The temperature is raised to 70° C. After 5 hours 204.18 gram (2.0 mol) PC is added and the temperature is raised to 100° C. The mixture is maintained at 100° C. for 30 minutes. Then, propanediol and excess of PC is removed in vacuo. The residue is washed with toluene, filtered and dried at 40° C. in vacuo. Obtained was a light brown, crystalline solid material (39.4 gram, 92%).

Preparation of the Bis Glycidylether of DPP

Compound 3

EXAMPLE I

A 250 ml autoclave was charged with 20.0 grams (46.7 mmol) of the bis-cyclic carbonate ester (I), 130 grams propyleneoxide (2.24 mol) and 3.75 grams ethyl triphenylphosphonium chloride (ETPPCl) (11 mmol). The mixture was heated to a 160° C. and maintained at this temperature for 16 hours. After cooling to room temperature the excess PO was evaporated and the formed propylene carbonate was removed in vacuum. The conversion was determined by NMR spectroscopy and proved to be 93%, about 7% carbonate end-groups remained unchanged. The selectivity was >98%, no ketone end-groups could be observed.

The remainder (15.8 gram) was dissolved in 40 ml MIBK and washed twice with 50 ml water.

Subsequently, the solution was treated with a 20 wt % aqueous NaOH solution for 1 hour. The phases were separated and the organic layer was washed with 50 ml of a 10% aqueous $NaH_2PO_4$ solution in water and subsequently twice with 50 ml water. After concentration in vacuum a brown resinous material was obtained. The epoxy group content was measured by titration and proved to be 5020 mmol/kg. The only side-products detectable in the NMR spectrum originated from residual catalyst.

EXAMPLE II

The same procedure as in example I was followed, but in this case the mixture was heated at 160° C. for 24 hours. The conversion proved to be almost complete. No ketone end-groups were observed. The work up was performed as indicated in example I. The epoxy group content proved to be 5180 mmol/kg.

EXAMPLE III

The same procedure as in example I was followed, but in this case the mixture was heated at 180° C. for 14 hours. The conversion proved to be almost complete. No ketone end-groups were observed. The work up was performed as indicated in example I. The epoxy group content proved to be 5050 mmol/kg.

EXAMPLE IV

A 250 ml autoclave, equipped with a magnetic stirrer bean, a thermocouple and a pressure meter was charged with 20.0 gram (46.7 mmol) of the bis-cyclic carbonate ester (1), 140 grams propyleneoxide (2.41 mol) and 4.26 grams ethyl triphenylphosphonium bromide (11 mmol). The mixture was heated to a 160° C. and maintained at this temperature for 16 hours. After cooling to room temperature the excess PO was evaporated and the formed propylene carbonate was removed in vacuum. The remainder (15.6 gram) was worked up as described in example I. The conversion was about 85%. The epoxy group content was 4920 mmol/kg.

EXAMPLE V

A 250 ml autoclave was charged with 20.0 grams (46.7 mmol) of the bis-cyclic carbonate ester (1), 130 grams propyleneoxide (2.24 mol) and 5.61 grams ethyl triphenylphosphonium iodide (11 mmol). The mixture was heated to a 140° C. and maintained at this temperature for 16 hours. After cooling to room temperature the excess PO was evaporated and the formed propylene carbonate was removed in vacuum. The conversion proved to be about 60%. The reaction is less selective, about 8% of the epoxy groups are transformed into ketone end-groups. Performing the reaction for 74 hours resulted in 80% conversion.

EXAMPLE VI

The same procedure as in example I was followed, however in this case tetramethylammonium chloride (TMAC) was used. Thus, 1.2 gram (11 mmol) TMAC was added instead of ETPPCl. With this catalyst the reaction appeared to be more sluggish. The obtained conversion at 160° C. in 16 hours was about 74%. Also the selectivity was some lower, about 90%. No ketone end-groups could be detected. Sideproducts are mainly due to reaction of amines with epoxy groups.

EXAMPLE VII

A 250 ml autoclave was charged with 20.0 grams (46.7 mmol) of the bis-cyclic carbonate ester (1), 150 grams propyleneoxide (2.58 mol) and 4.06 grams ethyl tris(ortho-tolyl)phosphonium chloride (11 mmol). The mixture was heated to a 160° C. and maintained at this temperature for 16 hours. After cooling to room temperature the excess PO was evaporated and the formed propylene carbonate was removed in vacuum. The work up was as described in example I.

EXAMPLE VIII

The same procedure as in example VII, but with ethyl tris(para-tolyl)phosphonium chloride (4.06 grams 11 mmol) as catalyst. The work up was as described in example I.

EXAMPLE IX

The same procedure as in example I, but with benzyltriphenylphosphonium chloride as the catalyst. The yields, conversion and selectivity were about the same. The epoxy group content was 5080 mmol/kg.

EXAMPLE X

The same procedure as in example I was followed, except that 1,3-propylenebis(triphenylphosphonium)dichloride (compound 2) was used as a catalyst (A bisphosphonium salt). The conversion was about 94%, the selectivity >98%. The work up was as described in example I. The epoxy group content of the resin was 5045 mmol/kg.

EXAMPLE XI

The same procedure as in example I, but with tris-orthomethoxyphenylphosphonium chloride as the catalyst. The yields, conversion and selectivity were about the same. The epoxy group content was 5080 mmol/kg.

EXAMPLE XII (COMPARATIVE EXAMPLE)

Alternatively, it was tried to convert the bis-carbonate ester of DPP (compound 2) directly in the diglycidyl ether of DPP (compound 3), using the procedure described in JP-SHO-61-33180. The reaction was performed at 250° C. and a vacuum was applied. In the beginning of the reaction (first 25 minutes) the lowest pressure obtainable was 4 mbar due to $CO_2$ formation. Hereafter, the vacuum was 1 mbar. The temperature was raised to 270° C. About 50% of the material was distilled. NMR analysis of the distillate showed the presence of ketone end-groups instead of epoxy end-groups. The residue also contained ketone end-groups and oligomeric structures, no epoxy end-groups.

We claim:

1. A process for the manufacture of a compound having the general formula

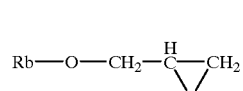

(D)

wherein Rb is:
(1) a group

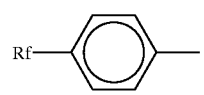

wherein Rf is hydrogen or a residue comprising one or more additional groups of the formula

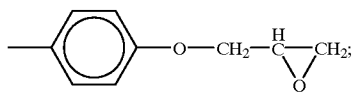

(2) a group Rj—(Q)ₐ-alkyl(Q)ₐ-, wherein the alkyl group is straight or branched and contains from 2 to 30 carbon atoms, wherein Q is aryl of from 6 to 20 carbon atoms or cycloalkyl from 6 to 20 carbon atoms and a and b are 0 or 1, wherein Rj is hydrogen or a residue comprising one or more additional groups of the formula:

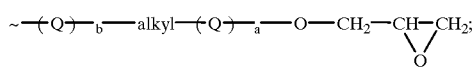

(3) a group

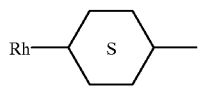

wherein Rh is hydrogen or a residue comprising one or more additional groups of the formula

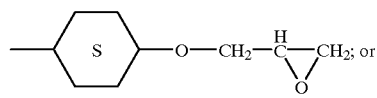

(4) a group

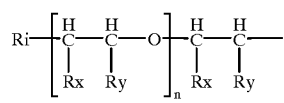

wherein Rx and Ry are hydrogen or only one of the symbols Rx and Ry is alkyl having from 1 to 4 carbon atoms, wherein n is an integer in the range of from 1 to 100 and Ri represents hydrogen or a residue comprising one or more additional groups of the formula

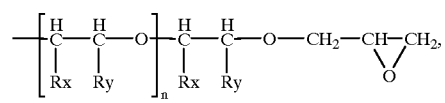

which comprises reacting a compound,

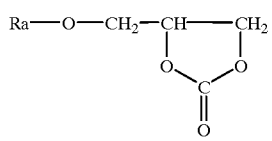

(A)

or

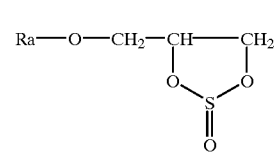

(B)

wherein Ra is (1) a group

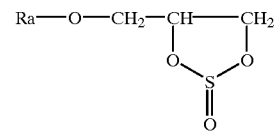

wherein Rp is hydrogen or a residue comprising one or more additional groups of the formula

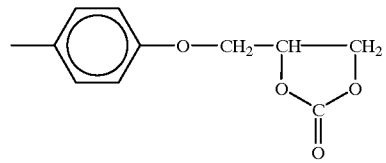

or

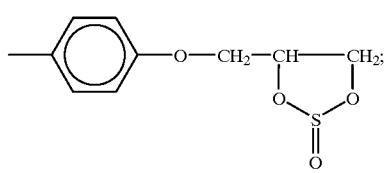

(2) a group Rq—(Q)ₐ-alkyl-(Q)ₐ- wherein the alkyl group is straight or branched and contains from 2 to 30 carbon atoms wherein Q is aryl of from 6 to 20 carbon atoms or cycloalkyl from 6 to 20 carbon atoms and a and b are 0 or 1, wherein Rq is hydrogen or a residue, comprising one or more additional groups of the formula

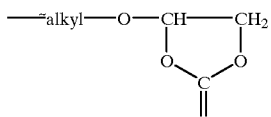

or

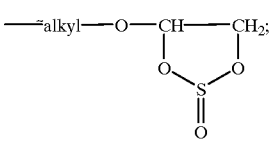

(3) a group

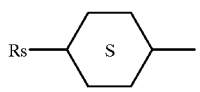

wherein Rs is hydrogen or a residue comprising one or more additional groups of the formula

[Structure: cyclohexyl-S-O-CH2-CH-CH2 with cyclic carbonate]

or

[Structure: cyclohexyl-S-O-CH2-CH-CH2 with cyclic sulfite (O-S(=O)-O)]; or (4) a group $$Rt\text{---}\left[\begin{array}{cc}H & H\\ \text{---}C\text{---}C\text{---}\\ Rx & Ry\end{array}\text{---}O\right]_n\text{---}\begin{array}{cc}H & H\\ C\text{---}C\text{---}\\ Rx & Ry\end{array}$$

wherein Rt is hydrogen or a group comprising:

$$\text{---}\left[\begin{array}{cc}H & H\\ C\text{---}C\\ Rx & Ry\end{array}\text{---}O\right]_n\text{---}\begin{array}{cc}H & H\\ CH\text{---}CH\text{---}O\text{---}CH_2\text{---}CH\text{---}CH_2\\ Rx & Ry\end{array}\begin{array}{c}\\ O\diagdown_C\diagup O\\ \|\\ O\end{array}$$

or $$\text{---}\left[\begin{array}{cc}H & H\\ C\text{---}C\\ Rx & Ry\end{array}\text{---}O\right]_n\text{---}\begin{array}{cc}H & H\\ CH\text{---}CH\text{---}O\text{---}CH_2\text{---}CH\text{---}CH_2\\ Rx & Ry\end{array}\begin{array}{c}\\ O\diagdown_S\diagup O\\ \|\\ O\end{array}$$

wherein Rx and Ry is hydrogen or only one of the symbols Rx and Ry is alkyl, having from 1 to 4 carbon atoms, wherein n is an integer from 1 to 100;

with alkylene oxide having from 1 to 20 carbon atoms, in the presence of a catalyst selected from the group of compounds consisting of at least one cation:

$$R_d\text{---}\underset{\underset{R_e}{|}}{\overset{\overset{R_c}{|}}{A(+)}}\text{---}R_g \quad (C)$$

wherein A represents nitrogen or phosphorus, wherein $R_c$, $R_d$ and $R_e$ each independently is an optionally substituted alkyl group having 1 to 10 carbon atoms or an optionally substituted phenyl group and wherein $R_g$ represents an alkyl group having from 1 to 6 carbon atoms which may optionally be terminally substituted by an aryl group or by a group of formula, $$R_d\text{---}\underset{\underset{R_e}{|}}{\overset{\overset{R_c}{|}}{A(+)}} \quad (C')$$

in combination with a counter anion $X^-$ selected from halogen, acetate, phosphate or carboxylate or combinations thereof.

2. The process of claim 1 wherein Rb is the group $R_j\text{-(Q-)}_{b}\text{-alkyl-(Q-)}_{a}$-~ wherein Q is phenyl or cyclohexyl.

3. The process of claim 1 wherein Rb represents a group, $$Ri\text{---}\left[\begin{array}{cc}H & H\\ C\text{---}C\\ Rx & Ry\end{array}\text{---}O\right]_n\text{---}\begin{array}{cc}H & H\\ C\text{---}C\text{---}\\ Rx & Ry\end{array}$$

wherein n is an integer in the range from 5 to 50.

4. The process of claim 1 wherein a catalyst (C) is used, wherein Rc, Rd and Re independently is an alkyl group having from 1 to 4 carbon atoms or a phenyl group optionally monosubstituted on the ortho place.

5. The process of claim 4 wherein the catalyst is ethyltriphenylphosphonium chloride, ethyltri(orthotolyl) phosphonium chloride or ethyl tri(phenyl)ammonium chloride.

6. The process of claim 5 wherein the catalyst is ethyltri (phenyl)phosphonium chloride.

7. The process of claim 1 wherein at least one compound of the formulae

[Structure (E): Rk-phenyl-O-CH2-CH-CH2 with cyclic carbonate]

or

[Structure (F): Rl-phenyl-O-CH2-CH-CH2 with cyclic sulfite]

wherein Rk represents a residue, comprising one or more additional groups of the formula

[Structure (E'): phenyl-O-CH2-CH-CH2 with cyclic carbonate]

and wherein Rl represents a residue comprising one or more additional groups of the formula (F')

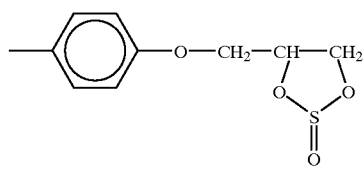

reacts with alkylene oxide having from 1 to 10 carbon atoms, in the presence of a catalyst, selected from the group of compounds containing at least one cation:

(C)

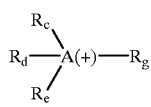

wherein A represents nitrogen or phosphorus, wherein $R_c$, $R_d$ and $R_e$ each independently is an optionally substituted alkyl group having 1 to 10 carbon atoms, or an optionally substituted phenyl group and wherein $R_g$ represents an alkyl group having from 1 to 6 carbon atoms which may optionally be terminally substituted by an aryl group or by a group of formula, (C')

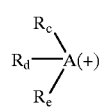

in combination with a counter anion $X^-$ selected from halogen, acetate, phosphate or carboxylate or combinations thereof, to form alkylene carbonate and a compound (D')

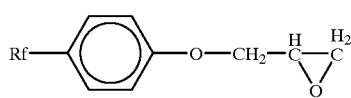

wherein Rf is hydrogen or a residue comprising one or more additional groups of the formula

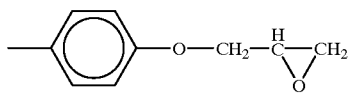

8. A process of preparing a composition comprising the steps of:

(a) converting propylene into propylene oxide, rearranging the propylene oxide into allylalcohol, and oxidizing the allylalcohol into glycidol, in the presence of a heterogeneous catalyst comprising at least a transition metal selected from a group consisting of titanium, vanadium and molybdenum, as such or in the form of a compound of said metals dispersed in a chemically inert carrier, or in the presence of a homogeneous catalyst formed by a dissolved or dispersed compound of said metals, (b) reacting a phenolic compound (I)

(I)

with glycidol

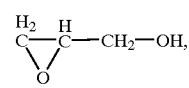
(II)

forming a di-α-glycol

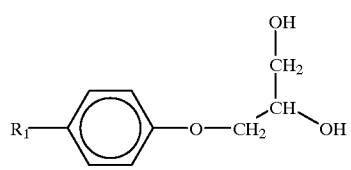
(III)

wherein R1 represents a residue comprising one or more additional groups of the formula

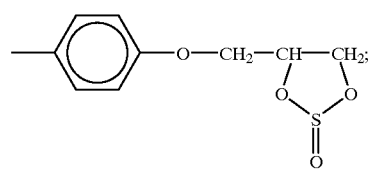
(F')

(c) reacting a di-α-glycol (III) with alkylenecarbonate, forming the compound

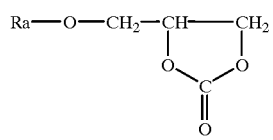
(A)

wherein Ra is (1) a group

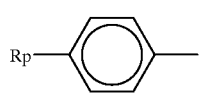

wherein Rp is hydrogen or a residue comprising one or more additional groups of the formula

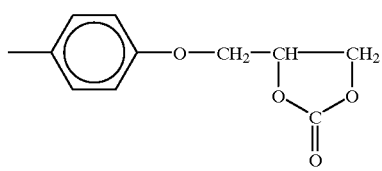

or

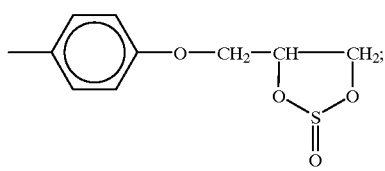

(2) a group Rq—(Q)ᵦ-alkyl—(Q)ₐ- wherein the alkyl group is straight or branched and contains from 2 to 30 carbon atoms wherein Q is aryl of from 6 to 20 carbon atoms or cycloalkyl from 6 to 20 carbon atoms and a and b are 0 or 1, wherein Rq is hydrogen or a residue, comprising one or more additional groups of the formula

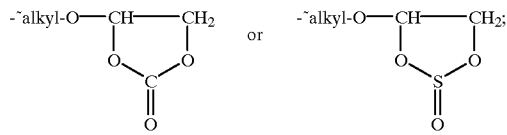

(3) a group

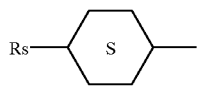

wherein Rs is hydrogen or a residue comprising one or more additional groups of the formula

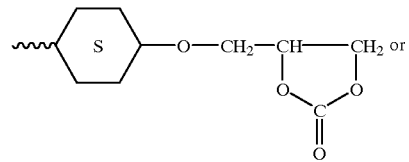

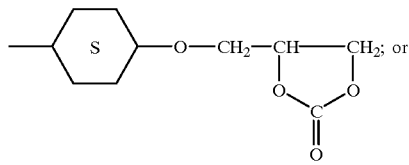

(4) a group

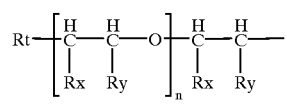

wherein Rt is hydrogen or a group comprising

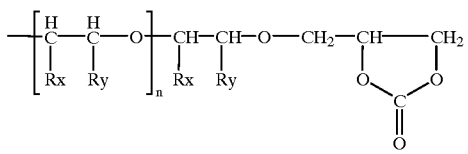

or

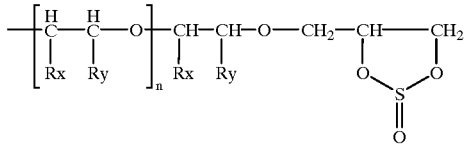

wherein Rx and Ry is hydrogen or only one of the symbols Rx and Ry is alkyl, having from 1 to 4 carbon atoms, wherein n is an integer from 1 to 100; and
(d) reacting compound (E) or (F)

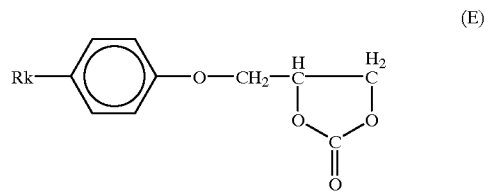   (E)

or

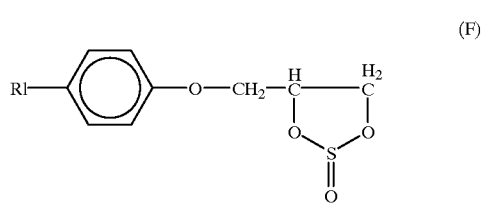   (F)

wherein Rk represents a residue, comprising one or more additional groups of the formula

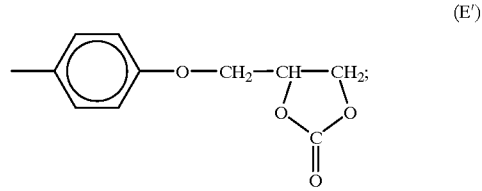   (E')

with alkylene oxide, having from 1 to 10 carbon, in the presence of a catalyst, selected from the group of compounds containing at least one cation:

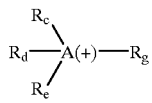   (C)

wherein A represents nitrogen or phosphorus, wherein $R_c$, $R_d$ and $R_e$ each independently is an optionally substituted alkyl group of from 1 to 10 carbon atoms or an optionally substituted phenyl group and wherein $R_g$ is an alkyl group having from 1 to 6 carbon atoms which may optionally be terminally substituted by an aryl group or by a group of formula

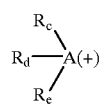
(C′)

together with a counter anion selected from halogen, acetate, phosphate or carboxylate or combinations thereof, to form alkylene carbonate or alkylene sulfite and a compound

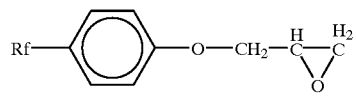
(D′)

wherein Rf is hydrogen or a residue comprising one or more additional groups of the formula

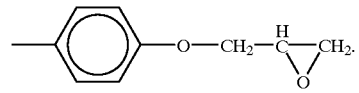

9. An epoxy resin produced by the process of claim 8 having a total halogen content in the range of from 300 to 1000 ppm.

* * * * *